US007776152B2

United States Patent
Hoke et al.

(10) Patent No.: US 7,776,152 B2
(45) Date of Patent: Aug. 17, 2010

(54) METHOD FOR CONTINUOUS, IN SITU EVALUATION OF ENTIRE WAFERS FOR MACROSCOPIC FEATURES DURING EPITAXIAL GROWTH

(75) Inventors: William E. Hoke, Wayland, MA (US); Theodore D. Kennedy, Derry, NH (US)

(73) Assignee: Raytheon Company, Waltham, MA (US)

( * ) Notice: Subject to any disclaimer, the term of this patent is extended or adjusted under 35 U.S.C. 154(b) by 0 days.

(21) Appl. No.: 11/555,470

(22) Filed: Nov. 1, 2006

(65) Prior Publication Data

US 2008/0098953 A1   May 1, 2008

(51) Int. Cl.
C30B 27/02 (2006.01)
C30B 15/00 (2006.01)
C30B 15/26 (2006.01)
C30B 15/30 (2006.01)

(52) U.S. Cl. .................. 117/14; 117/54; 117/85; 117/88; 117/89; 117/103; 117/104; 117/108; 117/201; 117/202; 117/203

(58) Field of Classification Search ......... 117/201–203, 117/14, 54, 85, 88–89, 103–104, 108
See application file for complete search history.

(56) References Cited

U.S. PATENT DOCUMENTS

| 3,409,481 A | * | 11/1968 | Leibenzeder et al. | 117/97 |
| 3,580,732 A | * | 5/1971 | Gukelberger Jr. et al | 117/77 |
| 3,607,463 A | * | 9/1971 | Kinoshita et al. | 117/59 |
| 3,737,739 A | * | 6/1973 | Blakeslee et al. | 257/506 |
| 4,144,116 A | * | 3/1979 | Jacob et al. | 117/91 |
| 4,945,254 A | | 7/1990 | Robbins | |
| 5,772,758 A | * | 6/1998 | Collins et al. | 117/85 |
| 6,325,850 B1 | | 12/2001 | Beaumont et al. | |

(Continued)

FOREIGN PATENT DOCUMENTS

EP   1743961   1/2007

(Continued)

OTHER PUBLICATIONS

NN9007177: IBM Technical Disclosure Bulletin, Jul. 1990, US, Uniform Array of Small Metal Balls.*

(Continued)

*Primary Examiner*—G. Nagesh Rao
(74) *Attorney, Agent, or Firm*—Daly, Crowley, Mofford & Durkee, LLP (57) ABSTRACT

Apparatus and method for growing and observing the growth of epitaxial layers on a wafer. The apparatus includes: epitaxial growth apparatus; a source of light mounted to illuminate an entire surface of the wafer in the apparatus during growth of the epitaxial layer on the entire surface of the wafer; and apparatus for observing scattering of the light from the entire surface of the wafer during growth of the epitaxial layer on the entire surface of the wafer. The method includes growing the epitaxial layer on a surface of the wafer and observing scattering of the light from the entire surface of the wafer during growth of the epitaxial layer on the entire surface of the wafer. The growing process is varied in accordance with the observation. With an epitaxial layer of gallium nitride (GaN) the entire surface of the wafer is observed for balls of gallium.

24 Claims, 5 Drawing Sheets

U.S. PATENT DOCUMENTS

| | | | |
|---|---|---|---|
| 6,521,042 B1 * | 2/2003 | Celii et al. | 117/201 |
| 6,596,079 B1 | 7/2003 | Vaudo et al. | |
| 2006/0201413 A1 | 9/2006 | Nishizawa | |
| 2008/0098953 A1 * | 5/2008 | Hoke et al. | 117/203 |
| 2009/0111250 A1 * | 4/2009 | Lee et al. | 438/483 |

FOREIGN PATENT DOCUMENTS

| | | |
|---|---|---|
| JP | 61-160046 | 7/1986 |
| JP | 61160046 | 7/1986 |
| JP | 4132942 | 5/1992 |
| JP | 04132942 | 7/1992 |
| WO | WO 2005 090650 | 9/2005 |

OTHER PUBLICATIONS

Sacilotti, M. et al, MOVPE growth of Ga 3D structures for fabrication of GaN materials, Journal of Crystal Growth 261 (2004) 253-258.*

Sacilotti, M. et al, Structural studies of nano/micrometric semiconducting GaInP wires grown by MOCVD, Journal of Crystal Growth 272 (2004) 198-203.*

International Search Report.

Written Opinion.

Notification Concerning Transmittal of International Preliminary Report on Patentability (Chapter 1 of the PCT), May 14, 2009, PCT/US2007/022214.

Written Opinion of the International Searching Authority, May 14, 2009, PCT/US2007/022214.

* cited by examiner

METHOD FOR CONTINUOUS, IN SITU EVALUATION OF ENTIRE WAFERS FOR MACROSCOPIC FEATURES DURING EPITAXIAL GROWTH

TECHNICAL FIELD

This invention relates generally to wafer evaluation and more particularly to methods for continuous, in situ evaluation of entire wafers for macroscopic features during epitaxial growth.

BACKGROUND AND SUMMARY

As is known in the art, epitaxial growth of semiconductor films, such as performed by molecular beam epitaxy (MBE) or metalorganic chemical vapor deposition (MOCVD) depends critically on the magnitudes and uniformities of reactant atoms on the substrate surface as well as the temperature and its uniformity across the substrate. In the specific example of plasma MBE growth of GaN, gallium atoms are evaporated onto the substrate surface in the presence of reactive nitrogen provided by a plasma source. The highest quality films are obtained when the net gallium beam flux (incoming gallium flux minus the gallium desorption rate) exceeds the reactive nitrogen beam flux resulting in a gallium adlayer on the growing surface. The gallium desorption rate from the surface is exponentially dependent on substrate temperature. If the adlayer does not exist, the surface will roughen with degraded material properties and will be visible as surface haze. When the net gallium beam flux exceeds the reactive nitrogen flux, an adlayer forms and begins to thicken, creating small gallium balls. Initially these small gallium balls are not an issue for material growth. If the gallium balls become too large, however, they will back-dissolve the substrate surface, resulting in surface roughening and will also interfere with the growth process. Therefore during growth the large gallium balls are periodically removed by interrupting the gallium and nitrogen beams, resulting in the large gallium balls to be desorbed from the substrate surface. Consequently at a given substrate temperature there is a growth window for gallium fluxes and growth times to obtain smooth surfaces without the formation of haze or large gallium balls. Surface haze can also form if the substrate surface is not atomically clean prior to growth since the surface crystallinity is disrupted leading to a rough surface.

Another issue encountered in epitaxial film growth on substrates requiring a backside coating for effective and uniform heating is the presence of pinholes in the coating. The occurrence of pinholes leads to substrate temperature non-uniformities in the vicinity of the pinhole and can perturb pyrometer readings.

One current technique for in situ monitoring the substrate surface for GaAs and GaN growth is RHEED (reflection high energy electron diffraction). In this technique, a focused high energy electron beam tangentially impinges on the substrate surface creating an electron diffraction pattern sensitive to surface stoichiometry. The RHEED intensity can also be used to monitor the build-up of evaporants on the surface. However, the inventors have recognized that the technique has important limitations. First, the RHEED beam samples only several square millimeters of a substrate surface that may be several inches in diameter. Consequently the impact of flux non-uniformities or temperature non-uniformities across the substrate is not characterized by RHEED. Growth conditions may be adjusted correctly inside the RHEED measurement area, but the conditions outside the probe area are unknown. This limitation becomes more serious with increasing wafer diameter not only due to the limited sample area but also the increased non-uniformity of film fluxes and substrate temperatures over larger areas. The inventors have also recognized that a second concern is that the RHEED high energy electron beam (typically 10-20 KeV) impinging on the substrate surface may alter the growth in this region. As a practical matter, the surface is monitored with RHEED less than 10% of the time to minimize any effect of the RHEED beam on material growth.

Other techniques are also available to provide in situ information of the growing film. One technique uses pyrometry to measure the substrate temperature. However the measurement area is less than 10% of the surface area of a 3-inch wafer. Ellipsometry has been used in other laboratories to provide in situ information. However its measurement area is again less than 10% of a 3-inch wafer.

The inventors have recognized that due to non-uniformities in beam fluxes and substrate temperature, a technique is needed to monitor the entire wafer for substrate scratches and polish damage, surface haze, metallic accumulations such as gallium balls, pinholes in metal coatings, and other macroscopic defects. Further a technique is needed to monitor wafers that are rotated to improve non-uniformities in beam fluxes and substrate temperatures. With such a technique, large gallium balls could be periodically eliminated during growth by adjusting growth conditions. Thus, GaN growth can be performed with excess gallium on the surface without the consequences of large gallium balls affecting the growth. Further, knowledge of the location and the appearance of haze during a run may assist in diagnosing the problem with the growth conditions and/or substrate preparation. The location and concentration of pinholes or other macroscopic defects also need to be characterized. Furthermore the relative temperature uniformity across the wafer can be determined as cold spots (reduced gallium desorption) lead to gallium balls and hot spots (enhanced gallium desorption) lead to haze.

Thus, in accordance with the invention, apparatus and method are provided for growing and observing the growth of epitaxial layers on a wafer. The apparatus includes: epitaxial growth apparatus; a source of light mounted to illuminate an entire surface of the wafer in the apparatus during growth of the epitaxial layer on the entire surface of the wafer; and apparatus for observing scattering of the light from the entire surface of the wafer during growth of the epitaxial layer on the entire surface of the wafer. The apparatus is suitable for stationary or rotating wafers.

The method includes growing the epitaxial layer on a surface of the wafer and observing the light scattered from the entire surface of the wafer during growth of the epitaxial layer on the entire surface of the wafer. The growing process is varied in accordance with the observation.

In one embodiment, the epitaxial layer is gallium nitride (GaN) and the entire surface of the wafer is observed for balls of gallium.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1:
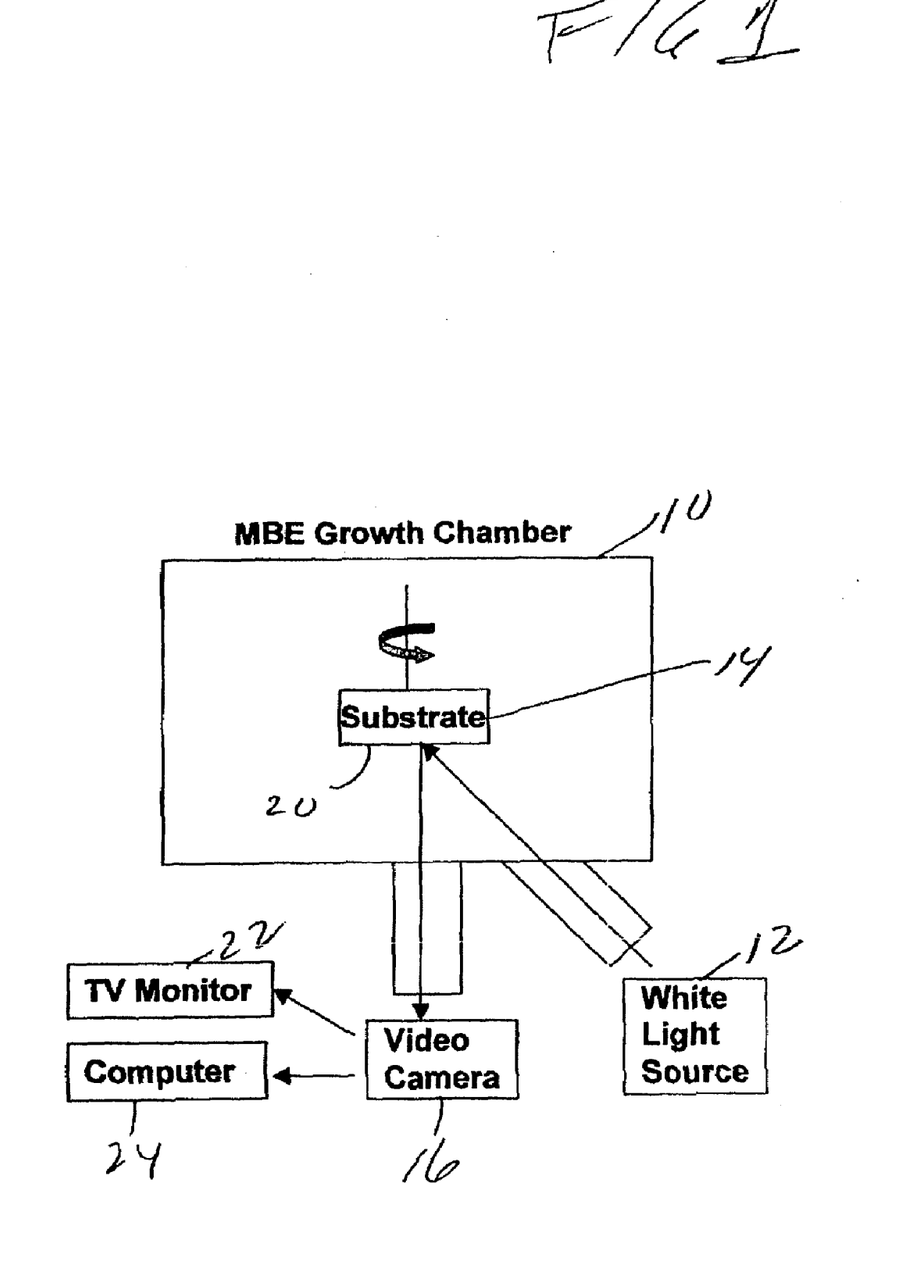
FIG. 1 is a schematic diagram of apparatus having a white light source illuminating the entire surface of a wafer wherein scattering of the light from the entire surface of the wafer is detected by a video camera positioned at a non-specular angle to a beam of wafer illumination, such camera being connected to a TV monitor for display and a computer for video capture according to the invention.
Figure 3A:
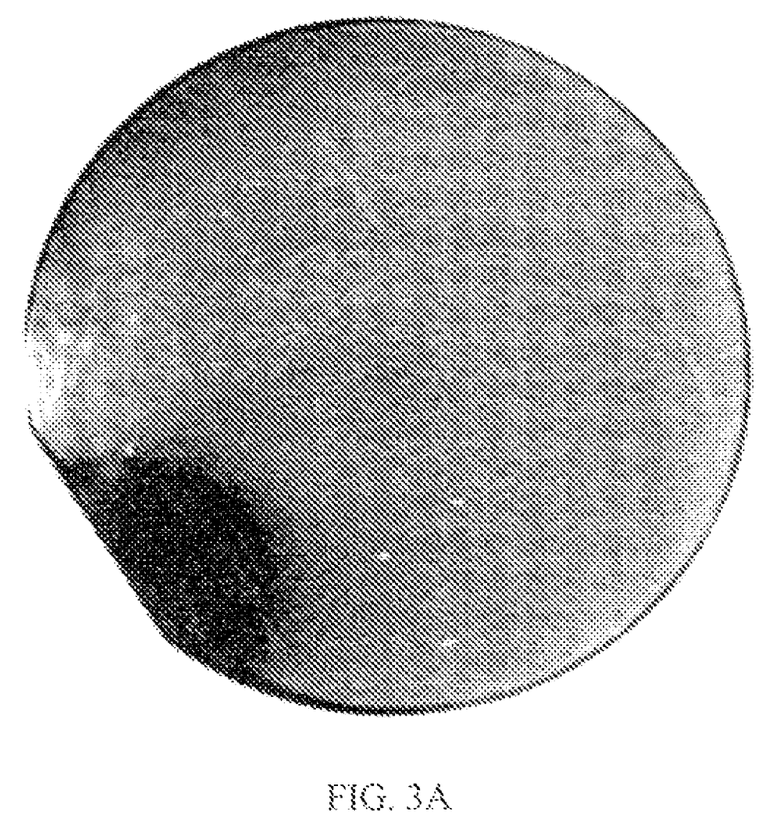
FIG. 3A is an image of the wafer of FIG. 1 produced by the TV monitor of FIG. 1 during epitaxial growth of a layer of GaN on the growth surface of the wafer in the MBE of FIG. 1, such image being taken in accordance with the invention, such image showing gallium balls (light area) formed during GaN growth on almost the entire 3-inch wafer except near the major flat; the picture was taken 30 minutes after the commencement of GaN growth.
Figure 3B:
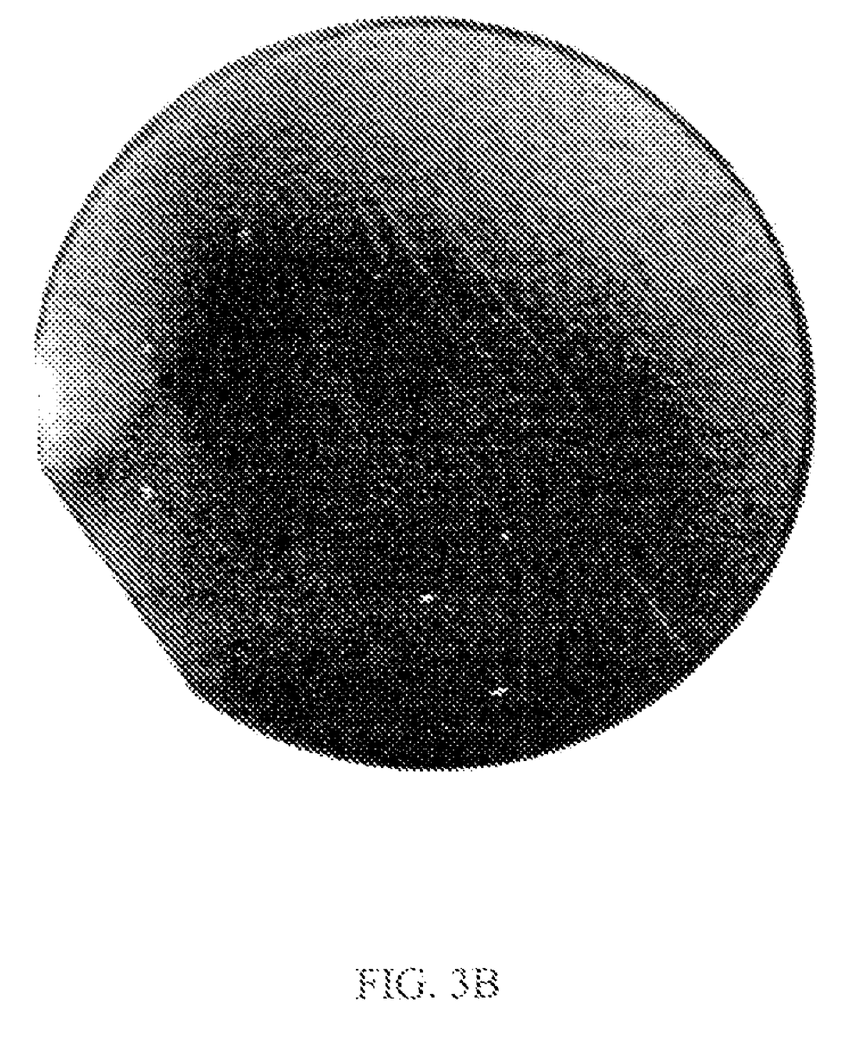
FIG. 3B is an image of the wafer of FIG. 1 produced by the TV monitor of FIG. 1 during epitaxial growth of a layer of GaN on the growth surface of the wafer in the MBE of FIG. 1, such image being taken in accordance with the invention, such image showing that by terminating the gallium and nitrogen beams during the epitaxial growth of the GaN most of the gallium balls have evaporated, it being noted that the bright spots on the wafer are due to pinholes in the backside metal coating.
Figure 3C:
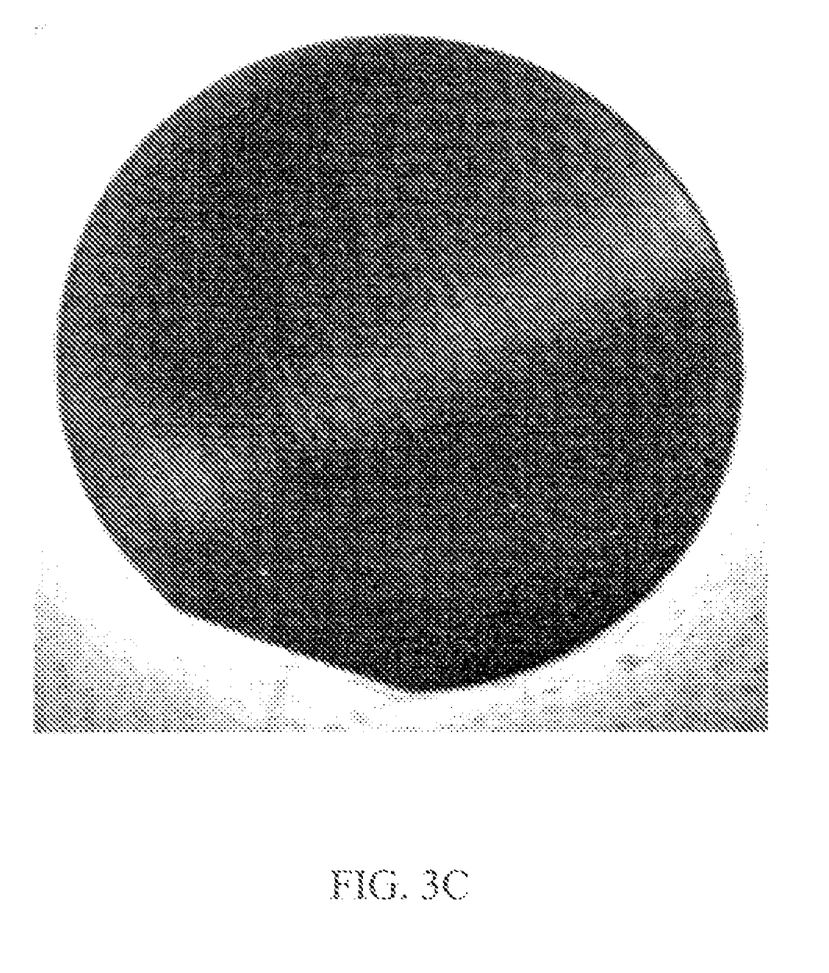
FIG. 3C is an image of the wafer of FIG. 1 produced by the TV monitor of FIG. 1 during epitaxial growth of a layer of GaN on the growth surface of the wafer in the MBE of FIG. 1, such image being taken in accordance with the invention, such image showing the gallium balls of FIG. 3C have been eliminated, the striations on the wafer being polishing scratches on the wafer backside.

Referring now to FIG. 1, a schematic of the invention incorporated on a molecular beam epitaxy (MBE) apparatus 10, here manufactured by VEECO model Gen 20 MBE is shown. Here white light source 12 (i.e., light over the entire visible spectrum) mounted to one flange of the MBE apparatus 10 is used to illuminate the entire growth surface of a wafer 14 or substrate, here for example, a 3-inch SiC wafer. A video camera 16 is mounted on another flange with nonspecular geometry to the light source 12. The viewing angle of the camera 16 is different from the angle of reflection of the axis of the beam of the light source 12 from the surface 20 of the wafer. The camera 16 is connected to a TV monitor 22 for viewing of the entire surface of the wafer and a computer 24 to capture images generated by the camera 16. When the growth surface 20 of wafer 14 is smooth the light specularly reflects off the surface 20 and is not significantly detected by the camera 16 resulting in a dark wafer image as shown in FIG. 3C. However, considering for example growth of GaN, gallium balls or haze (as shown on FIG. 3A) will scatter the white light from source 12 and will be detected by the camera 16. Consequently on the TV monitor 22 the areas of the wafer with haze or gallium balls will appear light on a dark background of the 3-inch wafer 14 (as shown on FIG. 3A). Pinholes in the substrate backside metal coating result in light from the substrate heater passing through the wafer and being detected by the camera.

Some key characteristics of this technique are:
1. The entire wafer can be continuously monitored throughout the entire growth process.
2. The wafer can be rotating or stationary.
3. Gallium balls have sub micron to micron sizes and can be distinguished from surface haze.
4. Large gallium balls can be periodically eliminated during growth by adjusting growth conditions. As shown in FIGS. 3A, 3B and 3C below, we have observed gallium balls during GaN growth and have eliminated them by changing growth conditions.
5. The technique is scalable for various wafer sizes.
6. The discussion above has focused on the MBE growth of column III-nitride films. However the invention is a general technique appropriate for the detection of surface haze, macroscopic imperfections, and metallic accumulations during MBE growth of almost any type of film (III-V, II-VI, IV-IV, etc.).
7. The invention does not require the UHV conditions of MBE (or any vacuum). Also the equipment is ex situ of the growth apparatus. Consequently it is appropriate for other epitaxial growth techniques such as MOCVD.
8. The camera observes scattered light, not reflected light. Therefore the angles of the light source to the camera are not critical other than not to be the specular angle. Furthermore neither the geometry of the light source or camera needs to be perpendicular to the growth surface. This flexibility of geometry is important for most growth apparatus that have limited options for window ports for observing the growing surface.

Figure 2:
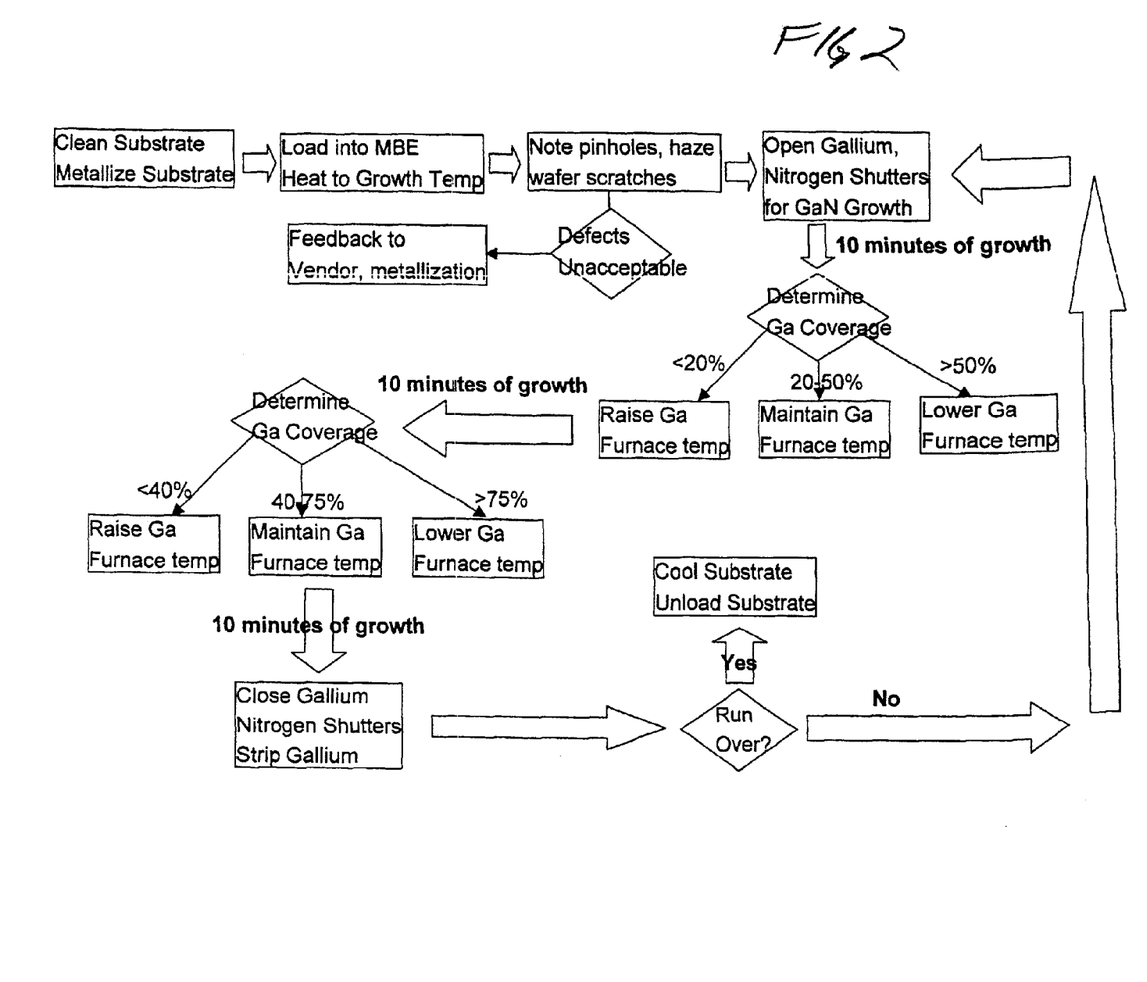
FIG. 2 is a flow diagram of a method for processing the substrate of FIG. 1 using the apparatus of FIG. 1 according to the invention.

Referring now to FIG. 2, the process for growing a gallium nitride epitaxial layer on wafer, here silicon carbide, for example. First the wafer is cleaned and the one surface, i.e., the back surface is metallized in any conventional manner. Next, the cleaned and metallized wafer is placed into the MBE. The wafer is heated to a predetermined epitaxial layer growth temperature.

With the light source illuminating the entire growth surface of the wafer, the images from the TV monitor of the entire growth surface of the wafer are observed by the operator for pinholes (visible from reflections from the metallized back surface of the wafer), haze and surface scratches. If pinholes, haze or wafer scratches are unacceptable, the wafer is rejected; otherwise the gallium and nitrogen shutters of the MBE are open to enable growth of the gallium nitride epitaxial layer. After about 10 minutes of growth, and the light source illuminating the entire growth surface of the wafer, the images from the TV monitor of the entire growth surface of the wafer are observed by the operator.

More particularly, the TV monitor is observed and the process is given in FIG. 2. The growth conditions are adjusted by raising or lowering the gallium flux (raise or lower gallium furnace temperature). For example, the TV monitor is examined after 10 minutes to determine what percentage of the surface is covered by gallium balls.

The area of the wafer surface covered by gallium balls is detected by observing the entire growth surface of the wafer during the epitaxial growth process. This area may be adjusted (increased or decreased) by adjusting growth conditions, as described above. Thus, the invention, in the particular case of MBE growth of GaN enables the detection of gallium ball formation, see FIGS. 3A and 3B.

More particularly, FIG. 3A is an image of the wafer of FIG. 1 produced by the TV monitor of FIG. 1 during epitaxial growth of a layer of GaN on the growth surface of the wafer in the MBE of FIG. 1, such image being taken in accordance with the invention, such image showing Gallium balls (light area) formed during GaN growth on almost the entire 3-inch wafer except near the major flat. FIG. 3A was taken after GaN growth had been performed for 30 minutes. FIG. 3B is an image of the wafer of FIG. 1 produced by the TV monitor of FIG. 1 during epitaxial growth of a layer of GaN on the growth surface of the wafer in the MBE of FIG. 1, such image being taken in accordance with the invention, such image showing that by terminating the gallium and nitrogen beams during the epitaxial growth of the GaN most of the gallium balls have evaporated, it being noted that the bright spots on the wafer are due to pinholes in the backside metal coating. FIG. 3C is an image of the wafer of FIG. 1 produced by the TV monitor of FIG. 1 during epitaxial growth of a layer of GaN on the growth surface of the wafer in the MBE of FIG. 1, such image being taken in accordance with the invention, such image showing the gallium balls of FIG. 3B have been eliminated, the striations on the wafer being polishing scratches on the wafer backside. As just described the gallium balls are removed by terminating the gallium and nitrogen beams. The gallium balls then evaporate from the growth surface.

If after 10 minutes of GaN growth the gallium ball coverage is less than 20 percent of the growth surface of the wafer, the gallium flux is increased by raising the gallium furnace temperature, if the gallium ball coverage is between 20 percent and 50 percent of the growth surface of the wafer, the temperature of the gallium furnace is maintained, and if the gallium ball coverage is greater than 50 percent of the growth surface of the wafer, the temperature of the gallium flux is lowered by lowering the gallium furnace temperature.

Next, after another 10 minutes of GaN growth; and the light source illuminating the entire growth surface of the wafer, the images from the TV monitor of the entire growth surface are observed by the operator. If the gallium ball coverage is less than 40 percent of the growth surface of the wafer, the gallium flux is increased, if the coverage is between 40 percent and 75 percent of the growth surface of the wafer, the gallium flux is maintained by maintaining the gallium furnace temperature, and if the coverage is greater than 75 percent of the growth surface of the wafer, the temperature of the gallium furnace is lowered resulting in a lowered gallium flux.

Next, after another 10 minutes, the gallium and nitrogen shutters are closed. The growth surface of the wafer is stripped of gallium by desorption.

Next, the process just described is repeated until the desired thickness is grown. Then the growth is terminated; the wafer is cooled and removed from the machine.

Performance Demonstration

Screen shots from a GaN HEMT run are shown in FIGS. 3A, 3B and 3C. In FIG. 3A, gallium balls have formed during 30 minutes of growth on almost the entire wafer. The net gallium growth flux was higher than the reactive nitrogen flux resulting in excess gallium accumulating on the surface which forms gallium balls. The gallium balls scatter the light, some of which reaches the video camera. Consequently the light areas indicate the location of gallium balls. Before the gallium balls could become too large and damage the surface, the gallium and nitrogen growth fluxes were then terminated for only 2-3 minutes to permit the excess gallium on the substrate surface to evaporate. FIG. 3B shows that most of the gallium has evaporated. FIG. 3C shows the subsequent surface at the start of the next GaN growth cycle with no gallium balls yet formed. FIGS. 3A and 3B also exhibit the presence of pinholes in the backside metal coating. The pinholes appear as bright spots since light from the glowing substrate heater is passing through the backside metal and is being detected by the video camera.

The following features are provided by the invention: 1. The entire wafer can be continuously monitored throughout the growth process; 2. The wafer can be stationary or rotating; 3. The invention detects gallium balls, even when they have just formed; 4. Large area wafers (we monitor a 5-inch platen) can be inspected; and 5. The technique is an in situ technique not limited to MBE and not limited to a vacuum chamber. It could be used on other growth processes such as MOCVD.

The invention provides a significant improvement in epitaxial growth monitoring and optimization. The technique enables optimization of material quality and uniformity across an entire wafer (not just a portion of a wafer provided by other techniques) and is an important growth feedback mechanism. Optimizing material quality and uniformity across the entire wafer is important for maximizing the yield and performance of semiconductor devices.

A number of embodiments of the invention have been described. Nevertheless, it will be understood that various modifications may be made without departing from the spirit and scope of the invention. For example, while the invention has been described for growing GaN, it may be used to observe the growth of other thin film materials such as AlGaN, InN, InGaN, AlInN, AlGaInN. Accordingly, other embodiments are within the scope of the following claims.

What is claimed is:

1. A method for forming and observing the growth of epitaxial layer on a wafer, comprising:
   growing the epitaxial layer on a surface of the wafer;
   observing scattering of light from the entire surface of the wafer during growth of the epitaxial layer on the entire surface of the wafer; and
   adjusting the epitaxial layer growing conditions in accordance with an observed percentage of the surface of the wafer covered by the balls of an element of the epitaxial layer.

2. A method for forming and observing the growth of epitaxial layers on a wafer, comprising:
   growing the epitaxial layer on a surface of the wafer;
   observing scattering of light from the entire surface of the wafer during growth of the epitaxial layer on the surface of the wafer;
   wherein the epitaxial layer is gallium nitride (GaN) and wherein the entire surface of the wafer is observed for balls of gallium; and
   adjusting the epitaxial layer growing conditions in accordance with an observed percentage of the surface of the wafer covered by the gallium balls.

3. The method recited in claim 2 including rotating the wafer during the growing.

4. The method recited in claim 1 wherein the entire surface of the wafer is observed for balls of material used in the growing of the epitaxial layer.

5. The method recited in claim 4 wherein the observed scattering of the light from the entire surface of the wafer during growth of the epitaxial layer on the entire surface of the wafer comprises capturing an image of the entire surface of the wafer during growth of the epitaxial layer on the entire surface of the wafer.

6. The method recited in claim 5 including rotating the wafer during the growing.

7. The method recited in claim 1 wherein the balls are gallium.

8. The method recited in claims 1 wherein the epitaxial layer is GaN, AlGaN, InN, InGaN, AlInN, or AlGaInN.

9. The method recited in claim 8 illuminating the entire surface and observing the entire surface as such entire surface is illuminated.

10. A method for forming and observing the growth of epitaxial layers on a wafer, comprising:
    growing the epitaxial layer on a surface of the wafer; and observing scattering of light from the surface of the wafer during growth of the epitaxial layer to detect balls of material used in the growing of the epitaxial layer; and adjusting the epitaxial layer growing in accordance with an observed percentage of the surface of the wafer covered by the balls.

11. The method recited in claim 10 including rotating the wafer during the growing.

12. The method recited in claim 11 wherein the balls are gallium.

13. The method recited in claim 10 wherein the material is GaN, AlGaN, InN, InGaN, AlInN, or AlGaInN.

14. The method recited in claim 13 including rotating the wafer during the growing.

15. Apparatus for growing and observing the growth of an epitaxial layer on a wafer, comprising:
   epitaxial growth apparatus for receiving therein the wafer;
   a source of light mounted to concurrently illuminate an entire surface of the wafer in the apparatus during growth of the epitaxial layer on the entire surface of the wafer;
   apparatus observing scattering of the light from the entire surface of the wafer during growth of the epitaxial layer on the entire surface of the wafer.

16. The apparatus recited in claim 15 wherein the epitaxial growth apparatus includes molecular beam epitaxial apparatus.

17. The apparatus recited in claim 15 wherein the observing apparatus includes a video camera.

18. The apparatus recited in claim 17 wherein the video camera is positioned at a non-specular angle to a beam of wafer illumination.

19. The apparatus recited in claim 15 wherein the observing apparatus includes a TV monitor.

20. The apparatus recited in claim 15 wherein the observing apparatus includes a computer.

21. The apparatus recited in claim 15 wherein the light source is fixed relative to the epitaxial growth apparatus and wherein the wafer is supported on a support rotatable with respect to the epitaxial growth apparatus.

22. The apparatus recited in claim 21 wherein the apparatus observing scattering of the light from the entire surface of the wafer observes such scattering while the wafer rotates and while the entire surface of the wafer is concurrently illuminated by the light source.

23. Apparatus for growing and observing the growth of a layer on a wafer, comprising:
   layer growth apparatus for depositing material on the wafer during the growing with adjustable temperature growing conditions and for receiving therein the wafer;
   a source of light mounted to concurrently illuminate an entire surface of the wafer in the apparatus during growth of the layer on the entire surface of the wafer;
   apparatus concurrently observing scattering of the light from the entire surface of the wafer with the light source concurrently illuminating the entire surface during growth of the layer on the entire surface of the wafer to detect balls of material used in the growing of the layer on the surface of the wafer;
   wherein the temperature growing conditions of the apparatus are adjusted in accordance with an observed percentage of the surface of the wafer covered by the balls.

24. Apparatus for growing an observing the growth of an epitaxial layer on a wafer, comprising: epitaxial growth apparatus for receiving therein the wafer; a source of light mounted illuminate an entire surface of the wafer in the apparatus during growth of the epitaxial layer on the entire surface of the wafer; apparatus concurrently observing light reflected at a plurality of different angles from the surface of the wafer during growth of the epitaxial layer on the surface of the wafer.

* * * * *